United States Patent
Cho et al.

(10) Patent No.: US 7,968,604 B2
(45) Date of Patent: Jun. 28, 2011

(54) PHARMACEUTICAL COMPOSITION FOR PREVENTION AND TREATMENT OF DRUG OR ALCOHOL ADDICTION OR BIPOLAR DISORDER USING SODIUM PHENYLBUTYRATE

(76) Inventors: Jeong-Woo Cho, Daejeon (KR); Sang-Rak Choi, Daejeon (KR); Sun-Gwan Hwang, Daejeon (KR)

( * ) Notice: Subject to any disclaimer, the term of this patent is extended or adjusted under 35 U.S.C. 154(b) by 0 days.

(21) Appl. No.: 11/992,211

(22) PCT Filed: Aug. 30, 2006

(86) PCT No.: PCT/KR2006/003412
§ 371 (c)(1), (2), (4) Date: Feb. 19, 2009

(87) PCT Pub. No.: WO2007/035029
PCT Pub. Date: Mar. 29, 2007

(65) Prior Publication Data
US 2009/0221714 A1  Sep. 3, 2009

(30) Foreign Application Priority Data
Sep. 23, 2005 (KR) .................. 10-2005-0088935
Apr. 18, 2006 (KR) .................. 10-2006-0034994

(51) Int. Cl.
*A61K 31/12* (2006.01)
(52) U.S. Cl. ........ 514/678; 514/809; 514/810; 514/812; 514/282

(58) Field of Classification Search .................. 514/282, 514/809, 810, 812, 678
See application file for complete search history.

(56) References Cited

U.S. PATENT DOCUMENTS

| 6,362,226 B2 | 3/2002 | Phillips, III et al. |
| 6,372,938 B1 | 4/2002 | Burzynski et al. |
| 2004/0242570 A1* | 12/2004 | Nudelman et al. ......... 514/224.8 |
| 2006/0018921 A1 | 1/2006 | Levenson |
| 2006/0045912 A1* | 3/2006 | Truog ......................... 424/468 |

FOREIGN PATENT DOCUMENTS

WO      02090534      11/2002

OTHER PUBLICATIONS

Vonk, Ronald, et al, "Is Autoimmune Thyroiditis Part of the Genetic Vulnerability (or an Endophenotype) for Bipolar Disorder," Biol. Psychiatry, vol. 62, pp. 135-140 (2007).*
Nurco, David N., et al, "Differential Contributions of Family and Peer Factors to the Etiology of Narcotic Addiction," Drug and Alcohol Dependence, vol. 51, pp. 229-237 (1998).*

(Continued)

*Primary Examiner* — Jeffrey S. Lundgren
*Assistant Examiner* — Savitha Rao

(57) ABSTRACT

Provided is a pharmaceutical composition for prevention and treatment of drug or alcohol addiction or bipolar disorder, comprising sodium phenylbutyrate (PBA). The pharmaceutical composition for prevention and treatment of drug or alcohol addiction or bipolar disorder in accordance with the present invention provides effects capable of inhibiting increases in locomotor activity which is a behavioral indicator of drug or alcohol addiction or bipolar disorder, by controlling a level of a neurotransmitter via regulation of expression of a neurotransmitter transporter.

7 Claims, 7 Drawing Sheets

OTHER PUBLICATIONS

Core et al., "Impact of the putative differentiating agents sodium phenylbutyrate and sodium phenylacetate on proliferation, differentiation, and apoptosis of primary neoplastic myeloid cells," Clinical Cancer Research Oct. 1997 3; 1755.

Fibach et al, "Enhanced fetal hemoglobin production by phenylacetate and 4- phenylbutyrate in erythroid precursors derived from normal donors and patients with sickle cell anemia and beta-thalassemia," vol. 82, Issue 7, pp. 2203-2209, Oct. 1, 1993.

Kruh, J., Effects of sodium butyrate, a new pharmacological agent, on cells in culture; Molecular and Cellular Biochemistry 42, 65-82 (1982).

Prasad, K. N., Butyric Acid: a small fatty acid with diverse biological functions; Life Sciences. vol. 27, 1351-1358 (1980).

The extended European Search Report by the European Patent Office, issued on Aug. 31, 2010, in the European patent application No. 06798579.6.

Phiel et al., "Histone deacetylase is a direct target of valproic acid, a potent anticonvulsant, mood stabilizer, and teratogen," J. Biol. Chem. Sep. 28, 2001;276(39):36734-41.

Gurvich et al., "Histone Deacetylase Is a Target of Valproic Acid-Mediated Cellular Differentiation," Cancer Res Feb. 1, 2004 64; 1079.

Kang et al., "Life extension in Drosophila by feeding a drug," Proc Nati Acad Sci U S A. Jan. 22, 2002;99(2):838-43.

Ralph et al., "Valproate Attenuates Hyperactive and Perseverative Locomotor Behaviors in Dopamine Transporter Knockdown Mice," Society for Neuroscience Abstract, vol. 27, No. 1, 2001, p. 1432.

Chen et al., "Evidence for the Involvement of Extracellular Signal-regulated Kinase (ERK) Pathway in Mood Modulation," Society for Neuroscience Abstract Viewer and Itinerary Planner, vol. 2002, 2002, XP8125900.

Tomasiewicz et al., "Behavioral effects of short-term administration of lithium and valproic acid in rats," Brain Res. Jun. 6, 2006;1093(1):83-94. Epub May 9, 2006. XP8125908.

International Search Report and Written Opinion dated Nov. 21, 2006.

Burlina, A.B. et al., Long-term treatment with sodium phenylbutyrate in ornithine transcarbamylase-deficient patients. Molecul. Genet. Metab. 2001, vol. 72, pp. 351-355.

Resar, L.M. et al., Induction of fetal hemoglobin synthesis in children with sickle cell anemia on low-dose oral sodium phenylbutyrate therapy, J. Pediatr. Hematol. Oncol. 2002, vol. 24, No. 9, pp. 737-741.

Zhang, X. et al. Sodium 4-phenylbutyrate induces apoptosis of human lung carcinoma cells through activating JNK pathway. J. Cell. Biochem. 2004, vol. 93, No. 4, pp. 819-829 (2004).

Kim, Jeong-Hoon. et al. The metabotropic glutamate receptor antagonist (RS)-MCPG produces hyperlocomotion in amphetamine pre-exposed rats. Neuropharmacology 37, (1998) 189-197.

Ferguson, Sally A.et al. Prenatal exposure to the dopamine agonist SKF-3893 disrupts the timing of the initial response of the suprachiasmatic nucleus to light. Brain Research 858 (2000) 284-289.

Zavala, A.R., et al., Cocaine-induced behavioral sensitization in the young rat. Psychopharmacology (2000) 151:291-298.

Karler, Ralph, et al., Amphetamine behavioral sensitization and the excitatory amino acids. Brain Research, 537 (1990) 76-82 Elsevier.

Einhorn, Leslie C., et al. Electrophysiological Effects of Cocoaine in the Mesoaccumbens Dopamine System: Studies in the Ventral Tegmental Area. The Journal of Neuroscience, Jan. 1988, 8(1):100-112.

Dismukes, Key, et al., Efffects of Neuroleptics on Release of 3H-Dopamine from Slices of Rat Corpus striatum. Naunyn-Schmiedeberg's Arch. Pharmacol. 297, 23-29 (1977).

Robertson, H.A., Expression of the Immediate Early Gene f-fos in Basal Ganglia: Induction by Dopaminergic Drugs. Canadian Journal of Neurological Sciences. 1991, 18:380-383.

Kuczenski, Ronald, et al. Amphetamine, Cocaine, and Fencamfamine: Relationship between Locomotor and Stereotypy Response Profiles and Caudate and Accumbens Dopamine Dynamics. The Journal of Neuroscience, Sep. 1991, 11(9):2703-2712.

Pontieri, F.E., et al., Intraveneous cocaine, morphine, and amphetamine preferentially increase extracellular dopamine in the "shell" as copared with the "core" of the rat nucleus accumbens. Proc. Natl. Acad. Sci. USA vol. 92, pp. 12304-12308, Dec. 1995 Pharmacology.

Belmaker, R. H. MD., Medical Progress Bipolar Disorder. N Engl J. Med 351:5, Jul. 29, 2004. pp. 476-486.

Kupfer, David J. MD., The Increasing Medical Burden in Bipolar Disorder. JAMA, May 25, 2005-vol. 293, No. 20 (Reprinted).

Frey, Benicio N., et al., Effects of mood stabilizers on hippocampus BDNF levels in an animal model of mania. Life Sciences 79 (2006) 281-286.

Arban, Roberto, et al., Evaluation of the effects of lamotrigine, valproate and carbamazepine in a rodent model of mania. Behavioural Brain Research 158 (2005) 123-132.

Dackis, Charles, A., Clinical Implications of Cocaine-Induced Cortical Depression. Neuropsychopharmacology (2005) 30, 1033.

Spanagel, Rainer, et al., The clock gene Per2 influences the glutamatergic system and modulates alcohol consumption. Nature Medicine vol. 11, No. 1, Jan. 2005, pp. 35-42.

McClung, Colleen A., Regulation of dopaminergic transmission and cocaine reward by the Clock gene. PNAS, Jun. 28, 2005. vol. 102, No. 26, pp. 9377-9381.

Kenna, George A., Pharmacotherapy of alcohol dependence: Targeting a complex disorder. vol. 2. No. 1, 2005, pp. 71-78.

Herman, Barbara H., et al. Medications for the treatment of cocaine addiction: Emerging candidates. vol. 2. No. 1, 2005, pp. 87-92.

* cited by examiner

[Fig. 1]
(A)
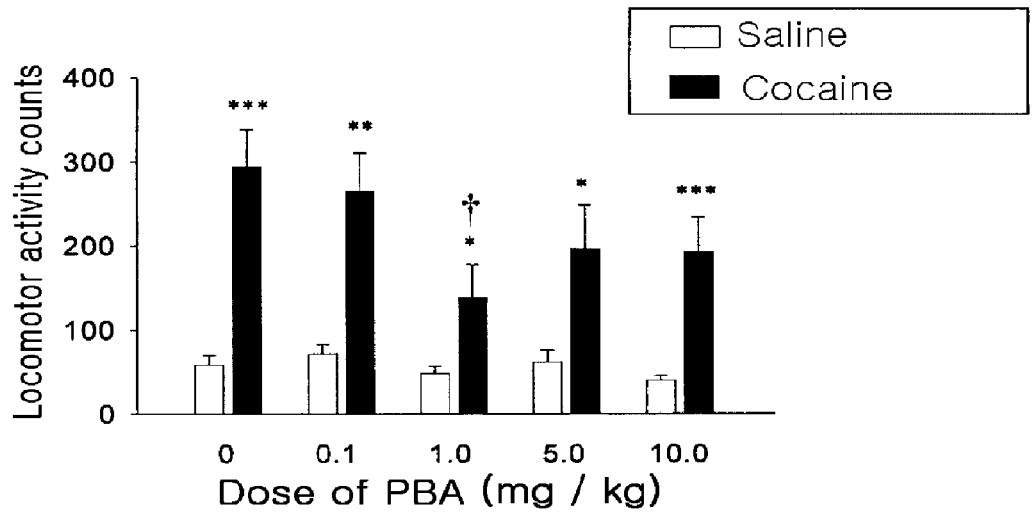
(B)
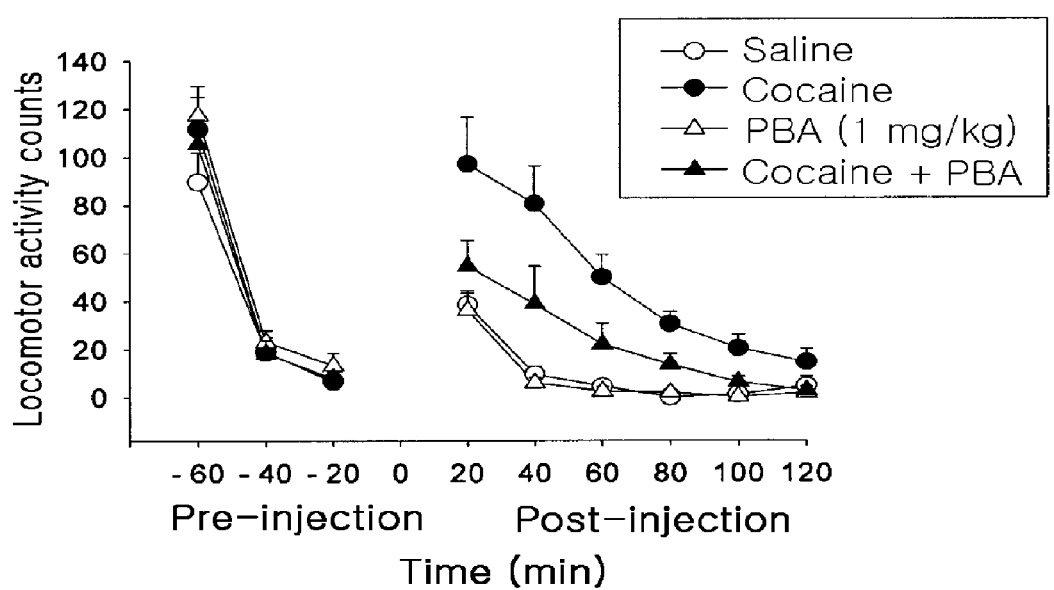

[Fig. 2]
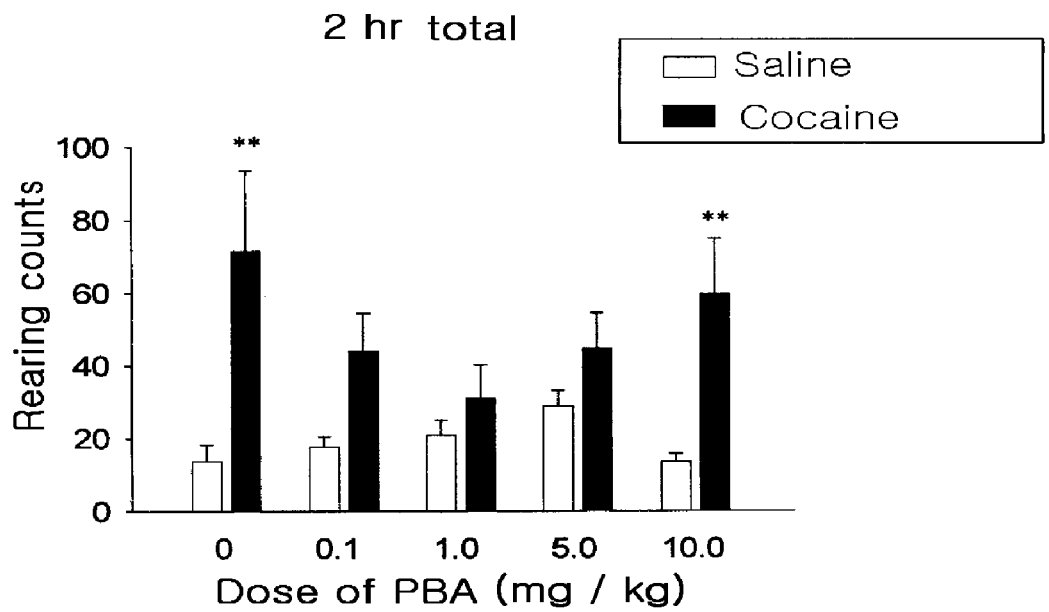
(A)
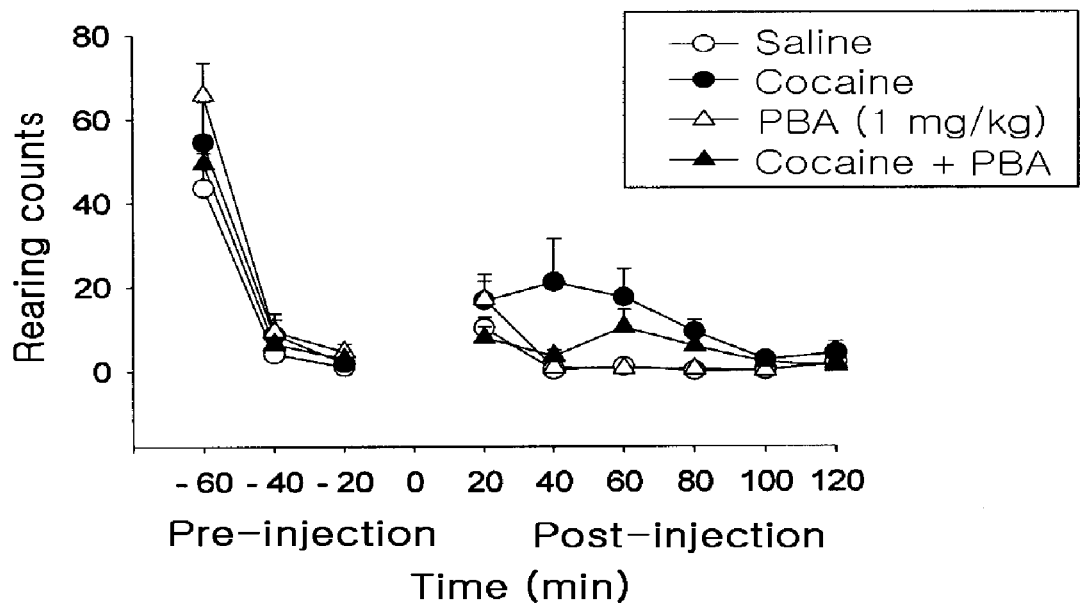
(B)

[Fig. 3]
(A)
2 hr total
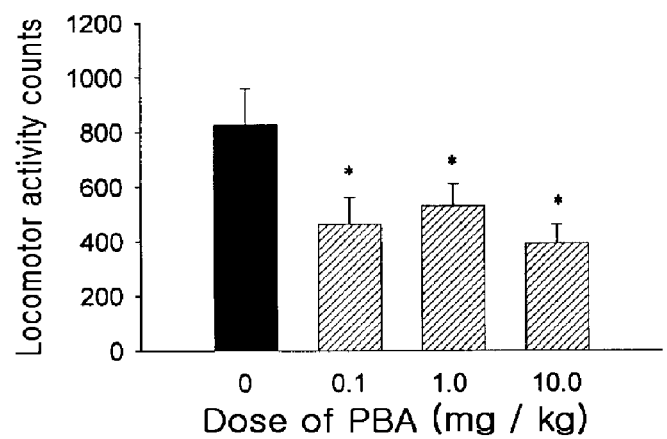
(B)
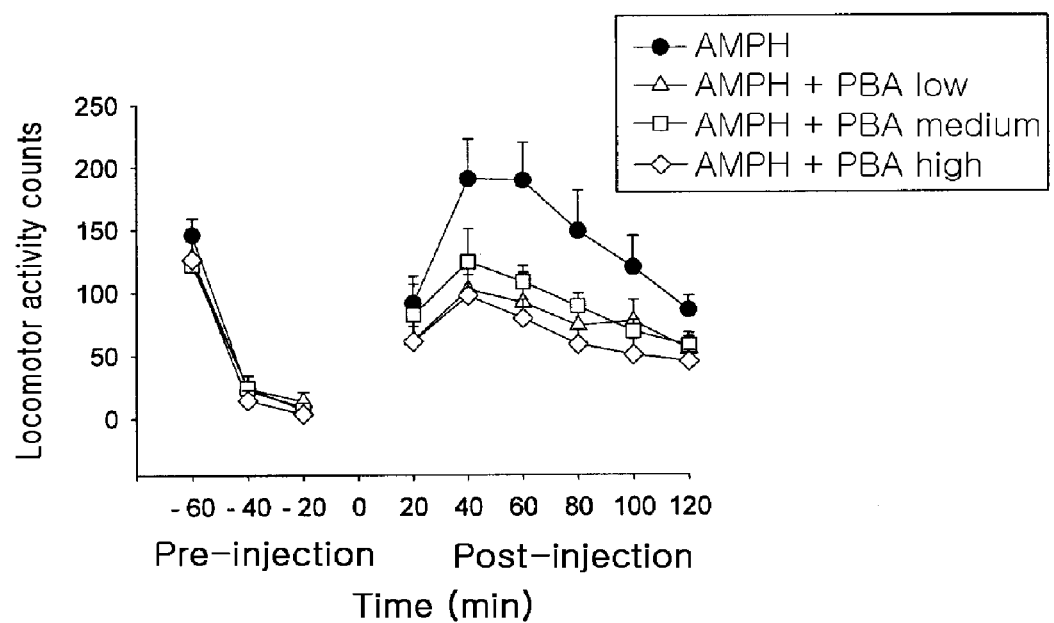

[Fig. 4]
(A)
2 hr total
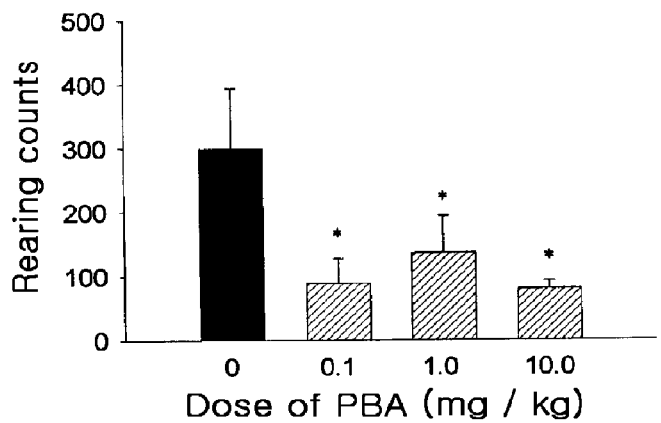
(B)
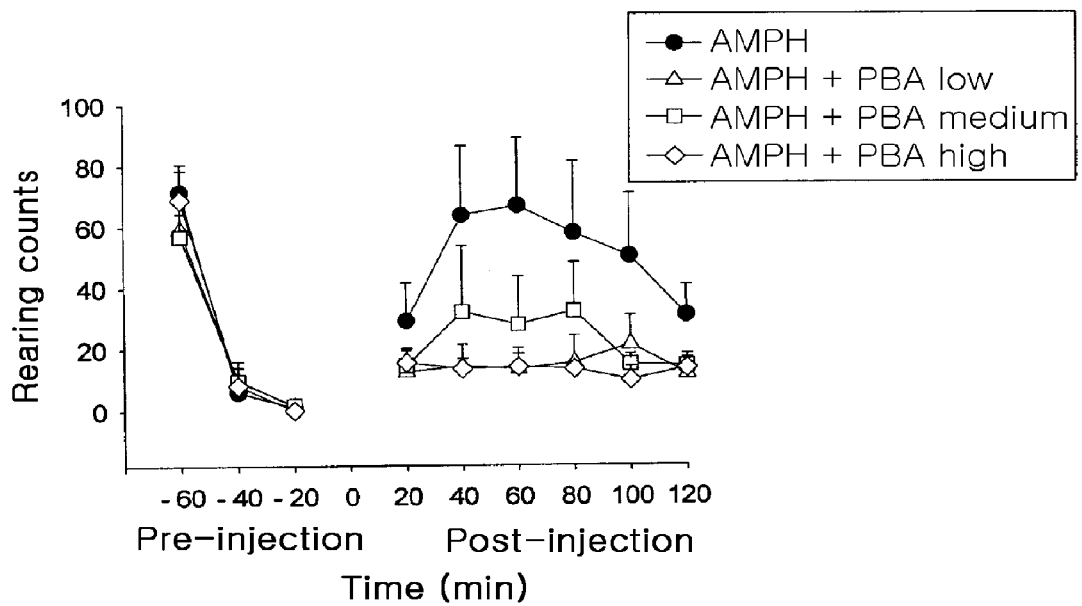

[Fig. 5]
(A)
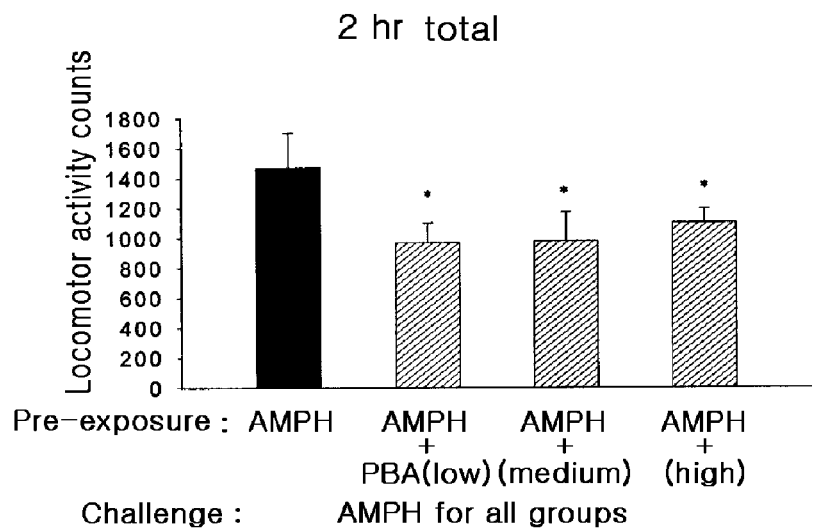
(B)
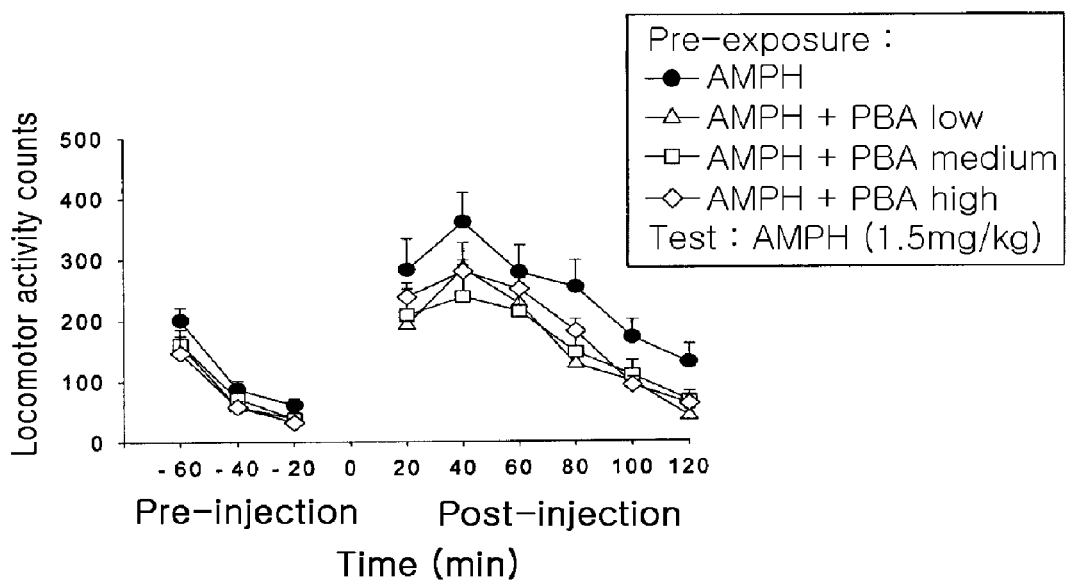

[Fig. 6]
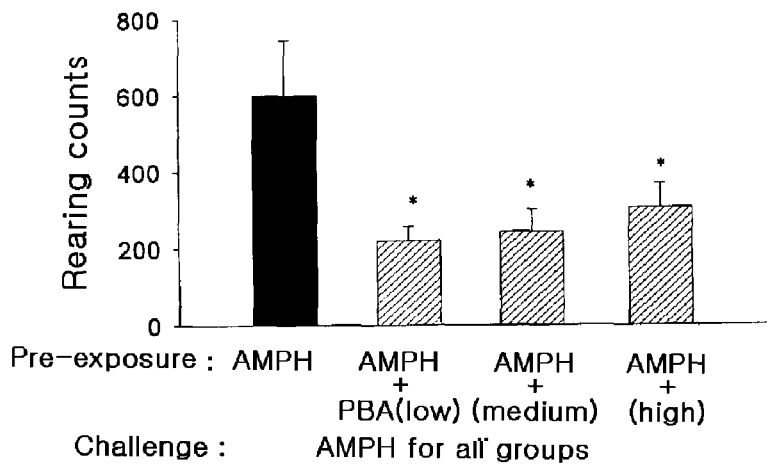
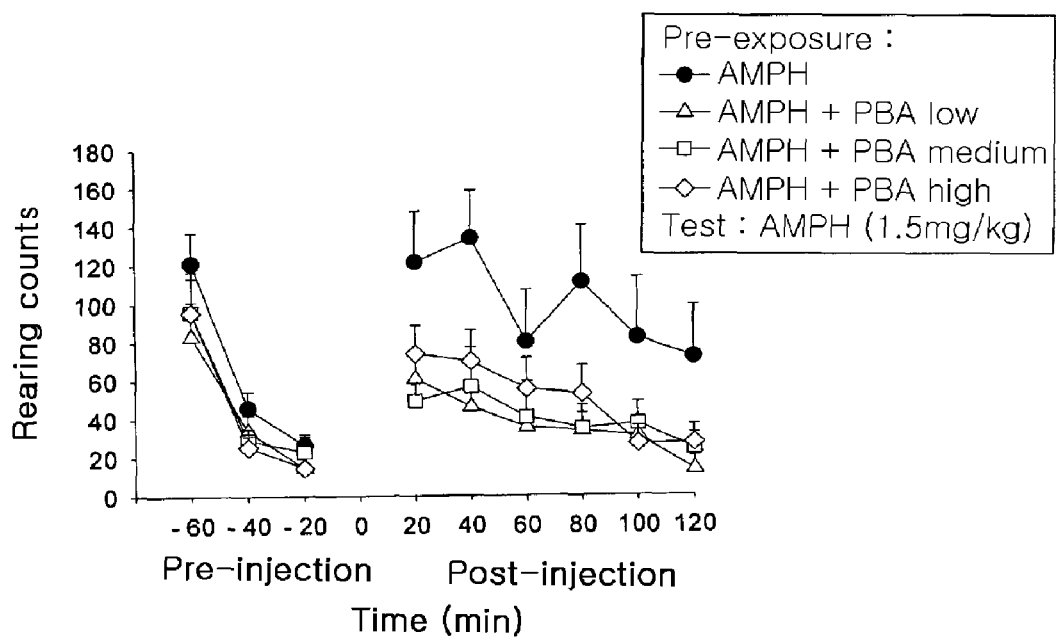

[Fig. 7]
(A)
2 hr total (Locomotor activity)
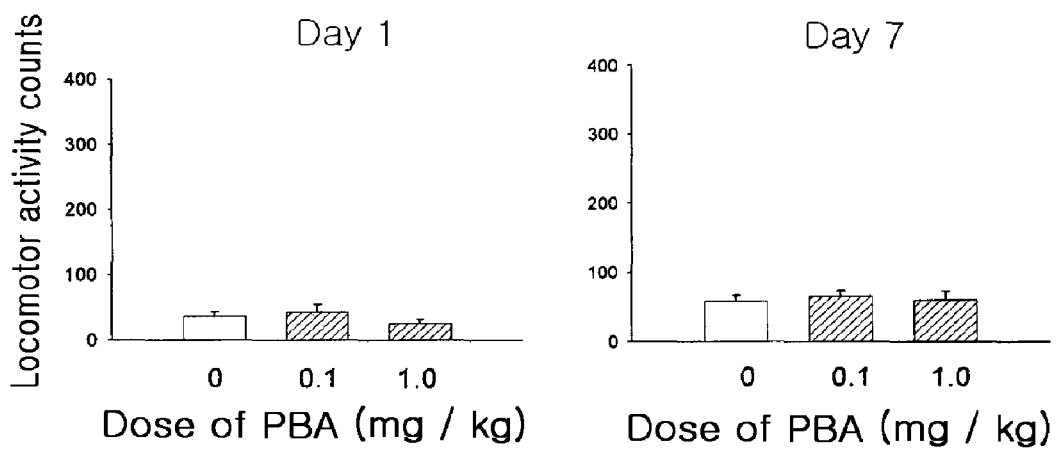
(B)
2 hr total (Rearing)
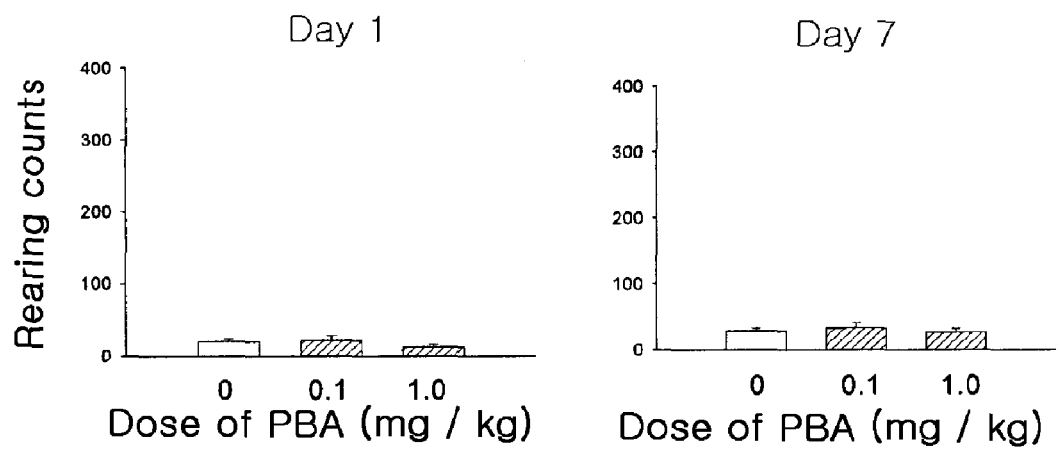

PHARMACEUTICAL COMPOSITION FOR PREVENTION AND TREATMENT OF DRUG OR ALCOHOL ADDICTION OR BIPOLAR DISORDER USING SODIUM PHENYLBUTYRATE

CROSS-REFERENCES TO RELATED APPLICATION

The present application is based on, and claims priority from, Korean Application Number 10-2005-88935, filed Sep. 23, 2005 and 10-2006-34994, filed Apr. 18, 2006, the disclosure of which are incorporated by reference herein in its entirety.

TECHNICAL FIELD

1. Field of the Invention

The present invention relates to a pharmaceutical composition for prevention and treatment of drug or alcohol addiction or bipolar disorder. More specifically, the present invention relates to a pharmaceutical composition for prevention and treatment of drug or alcohol addiction or bipolar disorder, using sodium phenylbutyrate as a novel use of a drug.

2. Background Art

Modern man, subjected to a variety of stresses in the course of daily life, is susceptible to drug addiction, and therefore drug or alcohol addiction is a major social problem.

As addictive drugs, mention may be made of narcotics such as morphine, cocaine and amphetamine, nicotine and alcohol. Among these drugs, addictive drugs such as narcotics cause users to become addicted, and stopping use thereof causes severe withdrawal symptoms, thus making normal life without drugs impossible and finally rendering persons physically and mentally debilitated leading to a high degree of risk.

For example, cocaine is an alkaloid drug derived from the leaves of the coca plant and is one of the most serious problem-causing narcotic drugs throughout the world. Cocaine is absorbed through mucous membranes of the nasal passage and acts on sensory nerve endings, thereby resulting in sensory paralysis, such as inhibiting pain and numbing the sense. Therefore, cocaine has been used as a local anesthetic in surgery and medical examination since 1862. Absorption of excessive amounts of cocaine or repeated use thereof causes cocaine poisoning, this in turn is accompanied by psychiatric disorders such as depression, anxiety, sleep disorders, chronic fatigue syndrome and mental confusion in conjunction with dystrophy.

Utilization of cocaine is usually effected via injection, intake and nasal inhalation thereof. A toxic dose of cocaine is 0.1 g and a lethal dose thereof is 1.0 g. Acute poisoning due to consumption of large amounts of cocaine begins with vertigo, facial pallor and mydriasis, thereby leading to intoxication, abalienation, visual and auditory hallucinations and syncope, finally causing dyspnea or cardiovascular collapse resulting in death. Cocaine addiction due to chronic use thereof is similar to morphine addiction, but exhibits pronounced physical exhaustion such as lethargy and weight loss and psychiatric problems such as difficulty in concentration and psychosomatic devastation. In addition, cocaine addicts may develop a specific form of cocaine hallucinosis such as tactile hallucinations, for example a disorder wherein the user experiences the sensation of crawling insects, worms, and other small animals on their skin.

In addictive drugs such as cocaine, medication thereof via repeated administration increases locomotor activity (Zavala A R, Nazarian A, Crawford C A, and Mcdougall S A, 2000). In addition, locomotor activity exhibits behavioral sensitization. Behavioral sensitization is a phenomenon in which repeated and intermittent administration of a small amount of an addictive drug produces gradual and incremental increases in locomotor activity and stereotype activity. Behavioral sensitization is divided into a development phase at which activity is gradually increased and an expression phase at which increased activity is maintained for extended periods of time (Karler R, Chaudhry I A, Calder L D, and Turkanis S A, 1990), and is used as an indicator of drug addiction.

Cocaine produces addiction via cocaine-induced reinforcing effects and the primary factor affecting such behavioral sensitization is activation of a dopamine (DA) neurotransmitter system. In particular, it is known that the midbrain-limbic system, in which A10 nerve, originating in the ventral tegmental area (VTA), projects into the nucleus accumbens (NAcc), plays an important role in compensation and reinforcing action due to cocaine administration (Einhorn L C, Johansen D A, and White F J, 1988). Cocaine primarily causes cardiovascular diseases via pharmacological action such as an increase of cardiac output, elevation of blood pressure and constriction of peripheral blood vessels (Foltin R W, and Fischman M W, 1988). In addition, cocaine administration elicits an increase in release of dopamine, a neurotransmitter, from the central nervous system, and thereby provides a pathogenic factor of drug addiction (Dismukes K, and Mulder A H, 1977). Such drug addiction results in mental disorders and is neurochemically caused by excessive release of dopamine from the nucleus accumbens (NAcc) and striatum region (Kreek M J, 1996).

Recent studies have reported increased expression of c-fos, an immediate early gene known as an indicator of neuroactivity, in projection regions of dopaminergic neuron cells such as the nucleus accumbens and striatum correlated with drug addiction, when neuroactivity is determined after cocaine administration (Robertson H A, Paul M L, Moratalla R, and Graybiel A M, 1991). In addition, when a D1 receptor agonist, SKF-38393, was repeatedly administered to experimental animals, expression of c-fos, an indicator of locomotor activity and neuroactivity, was inhibited (Sally A F, Shawn A R, Mdgorzata K, and David J K, 2000). Further, experimental evidence has been presented showing a close relationship between dopamine, which is a biochemical aspect, and locomotor activity, which is an ethological aspect (Kuczenski R, Segal D S, and Aizenstein M L, 1991). Experimental results via use of in vivo microdialysis have shown that cocaine administration remarkably increases dopamine concentrations in the striatum and nucleus accumbens related to drug addiction, and also increases locomotor activity (Pontieri F E, Tanda G, and Dichiara G, 1995).

Bipolar disorder (BD) is a major devastating psychiatric illness which is associated with suicide and loss of work productivity (Belmaker, 2004; Kupfer, 2005). The pathophysiology of bipolar disorder remains poorly understood despite advanced genetics, neurobiology and pharmacology. Benicio N. Frey et al (2006. Effects of mood stabilizers on hippocampus BDNF levels in an animal model of mania. Life Sciences, LFS-11196) have evaluated mood-stabilizing effects of lithium and valproate, via confirmation of animal behavior (locomotor activity) following co-administration of amphetamine (AMPH) with lithium or valproate which is a representative drug for the treatment of alcohol addiction. Further, Roberto Arban et al (2005, Evaluation of the effects of lamotrigine, valproate and carbazepine in a rodent model of mania. Behavioural Brain Research 158(2005) 123-132) have reported that lamotrigine, valproate and carbamazepine decreases amphetamine-induced behavioral activity, by measuring the moved distance of an experimental animal following co-administration of amphetamine with lamotrigine, valproate and carbamazepine.

Meanwhile, sodium phenylbutyrate (PBA) is a well-known chemical compound, and therapeutically applicable field and usage of PBA reported hitherto will be illustrated hereinafter.

Sodium phenylbutyrate (PBA) has been conventionally reported to reduce generation of harmful ammonia by decreasing glutamine levels. Ammonaps$^R$ is currently on the market as a therapeutic drug for the treatment of urea cycle disorders, containing sodium phenylbutyrate as a main ingredient.

In addition, phenylbutyrate has been reported to be effective in treatment of autism by acting as a glutamine level-reducing agent. That is, it is reported that since autistic patients exhibit abnormally higher levels of glutamine and glycine, it is possible to treat autism by decreasing glutamine levels via reduction of a level of glutamate, which is a precursor of glutamine and is an excitotoxic amino acid, through administration of phenylbutyrate (U.S. Pat. No. 6,362,226).

Further, phenylbutyrate is known to have therapeutic effects on cystic fibrosis and tumors or cancers, but there still remains no report for therapeutic effects of phenylbutyrate on drug or alcohol addiction or bipolar disorder.

DISCLOSURE OF INVENTION

Technical Problem

Therefore, the present invention has been made in view of the above problems, and it is an object of the present invention to provide a pharmaceutical composition for prevention and treatment of drug or alcohol addiction or bipolar disorder, utilizing sodium phenylbutyrate (PBA) which is capable of inhibiting an increase of locomotor activity by controlling a level of a neurotransmitter via regulation of expression of a neurotransmitter transporter.

Technical Solution

In accordance with the present invention, the above and other objects can be accomplished by the provision of a pharmaceutical composition for prevention and treatment of drug or alcohol addiction or bipolar disorder, comprising sodium phenylbutyrate (PBA).

BRIEF DESCRIPTION OF THE DRAWINGS

The above and other objects, features and other advantages of the present invention will be more clearly understood from the following detailed description taken in conjunction with the accompanying drawings, in which:

FIG. 1 graphically shows the results of effects of sodium phenylbutyrate on cocaine-induced (acute) locomotor activity;

FIG. 2 graphically shows the results of effects of sodium phenylbutyrate on cocaine-induced (acute) rearing activity;

FIG. 3 graphically shows the results of effects of sodium phenylbutyrate on amphetamine-induced (acute) locomotor activity;

FIG. 4 graphically shows the results of effects of sodium phenylbutyrate on amphetamine-induced (acute) rearing activity;

FIG. 5 graphically shows the results of effects of sodium phenylbutyrate on amphetamine-induced (chronic) locomotor activity;

FIG. 6 graphically shows the results of effects of sodium phenylbutyrate on amphetamine-induced (chronic) rearing activity; and FIG. 7 graphically shows the results of effects of sodium phenylbutyrate on locomotor activity of animals when sodium phenylbutyrate alone is administered daily via intraperitoneal injection for 7 consecutive days.

BEST MODE FOR CARRYING OUT THE INVENTION

Hereinafter, the present invention will be described in more detail.

Sodium phenylbutyrate, which is used as a main ingredient in a pharmaceutical composition in accordance with the present invention, is represented by structural formula I as below:

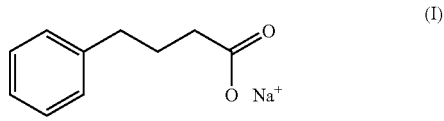

(I)

As a result of extensive investigation, the present inventors have found that sodium phenylbutyrate, which is currently used primarily as a therapeutic drug for treatment of urea cycle disorders, is therapeutically effective in treatment of drug or alcohol addiction or bipolar disorder as a novel therapeutic use. The present invention has been completed based on these findings.

Drug addictions that can be treated via application of the pharmaceutical composition in accordance with the present invention include, but are not limited to, amphetamine addiction and cocaine addiction. Repeated administration of an antihypnotic drug, such as amphetamine or cocaine, to animals tends to significantly increase locomotor activity, which is called behavioral sensitization. Such a phenomenon is known to provide a clue which is important in neurobiological elucidation of drug addiction.

In the present invention, effects of sodium phenylbutyrate on formation of behavioral sensitization due to administration of an antihypnotic drug, such as amphetamine or cocaine, were investigated and as a result, it was revealed that sodium phenylbutyrate inhibits an increase in locomotor activity which is a behavioral indicator of drug addiction, thus confirming that sodium phenylbutyrate has therapeutic effects on drug addiction.

Without wishing to be bound to any particular theory, it is believed that sodium phenylbutyrate, which is used as an active ingredient in the pharmaceutical composition in accordance with the present invention, controls a level of neurotransmitters such as glutamate, dopamine and gamma-aminobutyric acid (GABA), via regulation of expression of a neurotransmitter transporter. In particular, it is believed that sodium phenylbutyrate regulates expression of a Glu transporter.

Even though drug addiction tests in the present invention were carried out on cocaine and amphetamine, it is believed that the pharmaceutical composition in accordance with the present invention is also therapeutically effective in the treatment of alcohol addiction and bipolar disorder.

The fact that addictive drugs such as alcohol and cocaine, in addiction mechanisms thereof, are affected by neurotransmitters such as dopamine or glutamate in nuclear accumbens is known (Charles A. Dackis, 2005), thus representing that addiction to such drugs is controlled by very similar mechanisms therebetween, and it is considered that it is possible to control a level of neurotransmitters in the nuclear accumbens by regulating (or increasing) a mechanism of sodium phenylbutyrate, asserted in the present invention, i.e., expression of the transporters for such neurotransmitters. It was recently published in the scientific literature and scientific journals that expression of such transporters is linked to drug addiction. More specifically, it was reported that glutamate and dopamine transporters are involved in alcohol addiction (Spanagel R et al, Nat Med. 2005 January; 11(1):35-42) and cocaine addiction (Colleen A. McClung, PNAS. 2005 June; 28(102):9377-9381). In addition, in connection with most studies of drug addiction, clinical tests and experiments are carried out in conjunction with an alcohol addiction study and test. For example, referring to Drug Discovery Today: Therapeutic Strategies Vol. 2. No. 1, 2005, p 71-78 (George A. Kenna, "Pharmacotherapy of alcohol dependence: Targeting a complex disorder"), and Drug Discovery Today: Therapeutic Strategies, Vol. 2. No. 1, 2005, p 87-92 (Barbara H. Herman et al, "Medication for the treatment of cocaine addiction: Emerging candidates"), it can be seen that alcohol addiction and drug addiction tests are simultaneously carried out utilizing the same drug and it is shown that the same drug already used in the alcohol addiction test is also effective in the addiction test of the drug such as cocaine. That is, it was revealed to some degree that drugs such as cocaine and alcohol share similar addiction mechanisms, and therefore, it can be seen that development of new drugs are focused to prepare drugs capable of treating or preventing both drug and alcohol addiction taking advantage of such similar addiction mechanisms between different drugs. Further, as discussed hereinbefore, Benicio N. Frey et al (2006. Effects of mood stabilizers on hippocampus BDNF levels in an animal model of mania. Life Sciences, LFS-11196) have evaluated mood-stabilizing effects of lithium and valproate, via confirmation of locomotor activity of a rat following co-administration of amphetamine (AMPH) with lithium or valproate which is a representative drug for the treatment of alcohol addiction. As such, even though drug addiction tests on cocaine and amphetamine were primarily studied in the present invention, it is believed that the pharmaceutical composition in accordance with the present invention is also therapeutically effective in the treatment of alcohol addiction and bipolar disorder.

The pharmaceutical composition containing sodium phenylbutyrate in accordance with the present invention may be used in the treatment of drug or alcohol addiction or bipolar disorder and may also be used for prevention of drug or alcohol addiction or bipolar disorder. In addition, upon clinical administration, the pharmaceutical composition in accordance with the present invention may be administered orally, intraperitoneally, subcutaneously, etc. Additionally, a dose of the pharmaceutical composition in accordance with the present invention can be appropriately determined depending upon various factors such as age and symptoms of patients, dosage forms and kinds of drugs.

The pharmaceutical composition in accordance with the present invention may be formulated into various unit dosage forms such as tablets, soft and hard capsules, solutions and the like, by addition of pharmaceutically acceptable carriers, for example diluents such as lactose, lubricants such as magnesium stearate, binding agents such as polyvinylpyrrolidone and disintegrating agents such as calcium carboxymethylcellulose.

Even though a unit dose of the pharmaceutical composition in accordance with the present invention varies depending upon various factors such as severity of addiction and age of subjects, it may be generally in the range of 5 to 2000 mg, and preferably 10 to 1000 mg. As used herein, the term "unit dose" refers to a daily dose of the pharmaceutical preparation for adults which may be administered singly or as a divided dose once or several times a day. The pharmaceutical composition in accordance with the present invention is preferably given orally by administration of the unit dose as a single dose or divided dose once to three times a day.

MODE FOR THE INVENTION

Now, the present invention will be described in more detail with reference to the following examples. These examples are provided only for illustrating the present invention and should not be construed as limiting the scope and spirit of the present invention.

EXAMPLES

In order to examine effects of a pharmaceutical composition for prevention and treatment of drug or alcohol addiction or bipolar disorder containing sodium phenylbutyrate (PBA) in accordance with the present invention, the following animal experiments were carried out using Sprague-Dawley rats, weighing 250-275 g (upon arrival), (Samtaco Animal Breeding Company, Osan, Korea).

A bank of 12 activity boxes was used to measure locomotor activity of animals (Kim & Vezina, 1998). Each box (22×43× 33 cm) estimated locomotor activity from photo beam interruptions. Rats were placed in the activity boxes for a 1-hour habituation period. Then, these rats were administered with the respective dosages of the pharmaceutical composition and were immediately placed again in the activity boxes, and locomotor activity and rearing activity of rats were measured for additional 2 hours. Specifically, a computer was adapted to count locomotion of rats via photo beams installed on the top/bottom and right/left of the activity boxes, and such locomotion behavior of rats was confirmed for two hours. Rearing activity was also measured by counting upward/downward motion of rats via photo beams installed in the activity boxes. Herein, measurement of rearing activity, unlike measurement of locomotor activity to confirm movement of rats, serves to confirm rearing up on their hind legs while raising front legs (it is known that administration of addictive drugs to rats results in an increase in rearing behavior in conjunction with locomotor activity and that rats seldom rear except when they feed), which is used as an indicator to evaluate effects of drug addiction. For reference, Examples of the present invention are also provided to confirm therapeutic effects of a pharmaceutical composition of the present invention on drug or alcohol addiction as well as bipolar disorder. For example, Benicio N. Frey et al (2006. Effects of mood stabilizers on hippocampus BDNF levels in an animal model of mania. Life Sciences, LFS-11196) have conducted an experiment for evaluating mood-stabilizing effects of a drug, via confirmation of animal behavior (locomotor activity) after co-administration of amphetamine (AMPH) and a drug of interest, using an experimental method similar to the method employed in Examples of the present invention.

Example 1

Different concentrations (0.1, 1.0, 5.0 and 10.0 mg/kg) of sodium phenylbutyrate were intraperitoneally injected (acute) alone or in combination with cocaine (15 mg/kg) into rats, and locomotor activity and rearing of animals were measured for 2 hours. The results thus obtained are given in FIGS.

1 and 2. In FIGS. 1 and 2, an open bar represents administration of physiological saline+sodium phenylbutyrate, and a solid bar represents administration of cocaine+sodium phenylbutyrate. FIGS. 1A and 2A represent results for total 2 hours and FIGS. 1B and 2B represent results for a time course of 20 minute intervals. In FIGS. 1B and 2B, negative values on an x-axis represent a habituation period prior to administration of drugs and drugs are injected at a point zero (n=8-17).

As can be seen from FIGS. 1 and 2, sodium phenylbutyrate was shown to reduce an increase in cocaine-induced locomotor activity and rearing of rats in a dose-dependent manner, and such effects were greatest at a dose of 1.0 mg/kg.

Example 2

Similar to Example 1, different concentrations (0.1, 1.0 and 10.0 mg/kg) of sodium phenylbutyrate were intraperitoneally injected (acute) alone or in combination with amphetamine (1.5 mg/kg) into rats, and locomotor activity of animals was measured for 2 hours. The results thus obtained are given in FIGS. 3 and 4. FIGS. 3A and 4A represent results for total 2 hours and FIGS. 3B and 4B represent results for a time course of 20 minute intervals. In FIGS. 3B and 4B, negative values on an x-axis represent a habituation period prior to administration of drugs and drugs are injected at a point zero (n=7-8).

As can be seen from FIGS. 3 and 4, sodium phenylbutyrate was also shown to decrease an increase in amphetamine-induced locomotor activity, and such effects were similarly exhibited at a dose of 0.1 to 10.0 mg/kg.

Example 3

In order to examine effects of sodium phenylbutyrate on formation of behavioral sensitization, different concentrations (0.1, 1.0 and 10.0 mg/kg) of sodium phenylbutyrate were repeatedly administered in combination with amphetamine (1.5 mg/kg) into rats, a total of four times, at an interval of 2 to 3 days. Behavioral sensitization was confirmed by intraperitoneally injecting the same dose of amphetamine (1.5 mg/kg) into rats of all groups and measuring locomotor activity of animals for two hours, after pre-exposure of animals to amphetamine followed by provision of a one-week withdrawal period. The results thus obtained are given in FIGS. 5 and 6. FIGS. 5A and 6A represent results for total 2 hours and FIGS. 5B and 6B represent results for a time course of 20 minute intervals. In FIGS. 5B and 6B, negative values on an x-axis represent a habituation period prior to administration of drugs and drugs are injected at a point zero (n=7-8).

As can be seen from FIGS. 5 and 6, it was observed that sodium phenylbutyrate exhibits significant blocking effects against amphetamine-induced behavioral sensitization. Such effects were particularly strong at a dose of 0.1 to 1.0 mg/kg.

Example 4

This example was designed to measure changes in locomotor activity responses of animals to sodium phenylbutyrate when only two different concentrations (0.1 and 1.0 mg/kg) of sodium phenylbutyrate were intraperitoneally injected daily for 7 consecutive days. On day 1 and day 7 of drug administration, locomotor activity of animals was measured. The results thus obtained are given in FIG. 7. FIG. 7A represents results of 2 hour-locomotor activity of animals on day 1 and day 7 of drug administration and FIG. 7B represents results of rearing measurement.

As can be seen from FIG. 7, when sodium phenylbutyrate (0.1 and 1.0 mg/kg) was repeatedly administered once a day for a total of 7 days, it was found that administration of sodium phenylbutyrate alone does not result in any significant changes in locomotor activity of animals.

INDUSTRIAL APPLICABILITY

As apparent from the above description, the present invention provides a pharmaceutical composition for prevention and treatment of drug or alcohol addiction or bipolar disorder, utilizing sodium phenylbutyrate (PBA) which is capable of inhibiting an increase in locomotor activity that is a behavioral indicator of drug addiction, by controlling a level of a neurotransmitter via regulation of expression of a neurotransmitter transporter.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for the treatment of drug addiction comprising administering to a patient in need of such treatment an amount effective to control a level of a neurotransmitter via regulation of expression of a neurotransmitter transporter of a pharmaceutical composition comprising sodium phenylbutyrate (PBA) and at least one pharmaceutically acceptable carrier.

2. A method according to claim 1, wherein the neurotransmitter includes glutamate, dopamine and gamma-aminobutyric acid (GABA).

3. A method according to claim 1, wherein the composition is formulated into a unit dosage form for oral administration.

4. A method according to claim 3, wherein the unit dosage form is a tablet, a soft or hard capsule or a solution.

5. A method according to claim 3, wherein the unit dosage form contains 5 to 2000 mg of sodium phenylbutyrate.

6. A method according to claim 1, wherein the carrier is at least one component selected from the group consisting of a diluent, a lubricant, a binding agent, a disintegrating agent and a stabilizer.

7. A method according to claim 1, wherein the drug addiction is amphetamine or cocaine addiction.

* * * * *